United States Patent [19]
Kornberg et al.

[11] Patent Number: 5,512,295
[45] Date of Patent: Apr. 30, 1996

[54] SYNTHETIC LIPOSOMES FOR ENHANCED UPTAKE AND DELIVERY

[75] Inventors: Arthur Kornberg, Portola Valley; Celina Castuma, Palo Alto, both of Calif.

[73] Assignee: The Board of Trustees of the Leland Stanford Junior University, Stanford, Calif.

[21] Appl. No.: 337,632

[22] Filed: Nov. 10, 1994

[51] Int. Cl.$^6$ .................................................. A61K 9/127
[52] U.S. Cl. ......................... 424/450; 428/402.2; 264/41
[58] Field of Search ........................ 424/450; 428/402.2; 436/829; 264/4.1, 4.3

[56] References Cited

PUBLICATIONS

Hug and Sleight, "Liposomes for the Transformation of Eukaryotic Cells", *Biochem. Biophys. Acta.* 1097:1–17 (1991).

Szoka, "Comparative Properties and Methods of Preparation of Lipid Vesicles (Liposomes)", *Ann. Rev. Biophys. Bioeng.* 9:467–508 (1980).

Wilson, Cell 17, p. 77 May 1979.

Ostro Archives of Biochem & Biophy. 201 #2 p. 392 1980.

Gao Biochem. Biophys Res. Comm. 179 #1 p. 280 1991.

*Primary Examiner*—Gollamundi S. Kishore
*Attorney, Agent, or Firm*—Bertram I. Rowland

[57] ABSTRACT

Liposomes are prepared comprising a polyhydroxybutyrate calcium polyphosphate complex which provides for uptake of a desired component, particularly nucleotides and nucleic acids. The charged species may be introduced into the lumen of a liposome by incubating liposomes with a solution of the component of interest for sufficient time to provide for introduction of the component into the lumen of the liposome, followed by washing at diminished temperatures. The resulting liposomes may then be used as vehicles for delivery of the lumen component.

12 Claims, No Drawings

SYNTHETIC LIPOSOMES FOR ENHANCED UPTAKE AND DELIVERY

The development of the inventions described in the subject application was supported at least in part by grants from the National Institute of Health, grant number GM-07581 and HFSP, grant number RG174/91.

INTRODUCTION

1. Technical Field

The field of this invention concerns the preparation and use of liposomes.

2. Background

For many purposes, liposomes provide a useful vehicle for transport and delivery of a wide variety of substances. Since the liposomes have a lipophilic membrane, they are capable of maintaining polar and charged molecules within the lumen of the liposomes for extended periods of time. Furthermore, since the membrane can be formed with a wide variety of compositions, numerous useful characteristics can be imparted to the system. Alternatively, the membrane has a wide variety of organic functional groups, which may be used as sites for covalent linking, whereby the surface of the membrane may be modified for a variety of purposes. Because many molecules can be maintained in the lumen, the liposome can be used for delivery of a highly localized concentration of a particular compound. Furthermore, by employing ligands or receptors which are specific for a particular complimentary binding member, in vertebrate hosts, one can direct the liposomes to one or more sites in the vertebrate. In this manner, where the contents of the lumen may have adverse side effects, one may be able to minimize the side effects by releasing the lumen contents at the target site.

In addition, because of the membranous nature of the liposome, there is the opportunity to provide for fusion of the liposome with a cellular target. The Sendai virus has been used successfully as a fusogen agent.

In preparing liposomes, the liposome is prepared by sonicating a dispersion of the lipids to form the membrane and the lumen component, whereby liposomes are formed with the lumen component internalized. This means, however, that the concentration of the component in the lumen is based on the concentration of the liposome forming dispersion. Since, in many cases, one is restricted as to how much of the lumen component can be dispersed, this is a severe restriction on the amount of the component which can be delivered by the liposome.

Relevant Literature

Hug, P. and Sleight, R. G. (1991) Liposomes for the transformation of eukaryotic cells. Biochem. Biophys. Acta. 1097:1–17. Szoka, F. and Papahadjopoulos (1980). Methods for preparation of liposomes. Annu. Rev. Bioeng. 9m 467–508.

SUMMARY OF THE INVENTION

Liposomes, their methods of preparation and their use are provided, where the liposomes comprising a polyhydroxybutyrate calcium polyphosphate complex have enhanced permeability to ionic charged solutes, which allows for a regulation of the concentration of the solute in the liposome lumen. The liposomes may be used as vehicles for transporting and delivering solutes to target cells or tissues.

DESCRIPTION OF THE SPECIFIC EMBODIMENTS

Liposomes are provided comprising a lipid membrane and a poly-β-hydroxybutyrate (hereafter polyhydroxybutyrate) calcium polyphosphate complex. The liposomes are prepared in conventional ways using appropriate lamellar forming lipids and polyhydroxybutyrate in the presence or absence of the complex.

A wide variety of lamellar forming lipids may be employed, particularly phosphatidyl lipids. The lipids may be naturally occurring or synthetic. The lipids may be obtained by extraction of naturally occurring membranes, such as bacterial membranes, e.g. *E. coli, B. subtilis, S. cerevisiae*, or other unicellular microorganisms, or cells from higher organisms, such as vertebrates, where the cells may be platelets, red blood cells, or other convenient cellular source. The phophatidyl esters, may be mono- or diesters, where the polar head may be choline (lecithins) ethanolamine, inositol or serine. Sphingomyelin and cardiolipin are useful as well as gangliosides, cerebrosides, steroids, e.g. cholesterol, and the like. The fatty acids will primarily be aliphatic of from 6 to 30 carbon atoms, more usually of from about 12 to 18 carbon atoms, saturated or unsaturated, branched or straight chain.

In some instances it may be desirable to have aliphatic unsaturation, which is capable of modulating the physical properties of the liposomes.

The poly-hydroxybutyrate may be obtained from natural sources or synthesized. The polymer will usually be at least about 5 kD weight average molecular weight, usually at least about 10 kD and not more than about 60 kD, more usually not more than about 30 kD, conveniently in the range of about 10 to 20 kD weight average molecular weight. The polymer may be prepared in accordance with conventional ways for polymerization of carboxylic acid esters, using acid, base, carboxylic acid activating agents, e.g. carbodiimide, and the like. Polymerized β-hydroxybutyric acid can be obtained by extraction from bacteria, in accordance with known methods. See for example: Reusch, R. N., Hiske, T. W. and Sadoff, H. L. (1986) J. Bacteriol. 168, 553–562.

The poly-hydroxybutyrate calcium polyphosphate complex may be preprepared by precipitating calcium polyphosphate and poly-hydroxy butyrate. Commercially available calcium polyphosphate may be employed such as PolyP$_{60}$ (available from Sigma), where the polyphosphate will be characterized by enzymatic reactions (Wurst, H. and Kornberg, A. (1994) J. Biol. Chem. 269:10996–11001). A soluble source of calcium is combined with the polyphosphate, e.g. calcium chloride, where the calcium will be in substantial molar excess to the polyphosphate, generally being from about 1 to 10 times in excess, more usually from about 2 to 5 times in excess. An aqueous medium is conveniently employed and the resulting calcium polyphosphate precipitate may be isolated by using centrifugation. Concentrations of polyphosphate will generally range from about 0.1 to 1 mM, while the calcium salt will generally range from about 0.5 to 5 mM.

The salt is dried for about 12–24 hrs to eliminate the aqueous solvent. The poly-hydroxybutyrate and polyphosphate salt may then be combined in an appropriate organic medium generally at a molar ratio of about 5–1:1, usually about 2 to 1, conveniently in a volatile organic medium, such as a chloroform or other solvent which dissolves the polyhydroxybutyrate. The solvent may then be removed in vacuo at an ambient or elevated temperature, usually below about 50° C.

The lipids may be combined with the complex at a molar ratio (based on poly-hydroxybutyrate) of at least 10:1, preferably at least about 20:1 and not more than about 60:1, generally ranging from about 25–40:1. An appropriate volatile solvent may be employed, including any of the conventional solvents indicated above to provide for intimate mixing of the lipids and polyhydroxybutyrate. In addition to the solvents described above, other solvents include polar organic solvents, such as aromatic hydrocarbons, or functionalized aromatic hydrocarbons, e.g. halogen, oxy, amino, non-oxo-carbonyl, or the like.

The solvent is evaporated under nitrogen, and the dried film is combined with an appropriate aqueous medium for liposome formation. Various buffered solutions may be employed, where the buffer will be present in the range of about 10 to 200 mM at a pH in the range of about 5 to 10. The particular manner of making the unilamellar liposomes, in this case is by vortexing the mixture at 0°–4° C. and further filtration through polycarbonate membranes (0.1μ) under nitrogen pressure. Preparations of liposomes may be found in U.S. Pat. Nos. 4,565,696; 4,737,323; and 4,804,539.

If desired, various ligands or receptors may be covalently conjugated to lipids present in the membrane of the liposome. Techniques for covalent conjugation include coupled by amide linkage with an activated carboxyl group, where the carboxyl group may be activated using carbodiimide or by preparing an active ester, e.g. N-hydroxy succinimide. With active hydroxyl groups, ethers may be formed, by using active halogen or pseudohalogen. Alternatively, amino or hydroxyl groups may be conjugated with thiol derivatives, such as 3-(2'-pyridylthio)propionate, methyldithioacetic acid, dinitrophenylthioacetic acid, or the like.

Usually, the phospholipids, including derivatized and underivatized phospholipids, will be at least about 75 or more percent of the total lipid, more usually at least about 90%, and frequently 100%. Other types of lipids may be employed to provide for particular types of characteristics and properties of the liposome, such as enhanced stability, enhanced fusion with a membrane, and the like. Conveniently, the temperature at which the liposomes are formed will be ambient temperature, although temperatures in the range of 4° C. to 50° C. may be employed, if desired depending on the degree of unsaturation and the nature of the polar head. Where uniform size is desired, the liposomes may be extruded through a polycarbonate membrane having a selected uniform pore size generally ranging from about 0.1–1μ. Either unilamellar vesicles or multilamellar vesicles may be prepared, depending upon the purpose for the vesicles, the nature of the lumen component, sensitivity of the use of the liposome to leakage of the liposome, and the like.

The subject vesicles may be used for a wide variety of purposes, being vehicles or containers for a wide variety of compositions in the lumen. The component of the lumen may be a single compound or a combination of compounds, usually not more than about four different compounds. Thus, the subject vesicles may be used for drug delivery, for the treatment of a wide variety of indications. Thus, prodrugs and drugs may be employed, particularly where the lumen component is polar, particularly charged, where the charges may be positive, negative, or combinations thereof. Drugs which may find use include cytotoxic drugs, antiviral agents, antiallergenic agents, anti-inflammatory agents, antiproliferative agents, cholinesterase inhibitors, β-blockers, α-adrenergic agents, pain relievers, antibiotics, etc. In addition, nucleic acids may be employed, both single stranded and double stranded, where particularly as to the single stranded, the sequences may be antisense. In addition, various nucleic acid vectors may be employed, particularly viral vectors, such as adenovirus, papilloma virus, retroviruses, nucleic acid complex with recombinases, and the like. The nucleic acids may find use as gene therapy, as expression inhibitors, and studying physiological processes in vivo. The nucleic acids may be a single nucleotide, oligonucleotides of from about 2 to 50 bases or bp, or nucleic acids of 50 to 5000 bases or bp or more.

In many instances it will be desirable that the liposome be capable of fusing with a cell membrane. Therefore, various fusogens may be employed to enhance the fusion of the liposome with the cell target. Fusogens include Sendai virus, non-ionic detergents, and the like. The fusogens may be coated onto the vesicles after the preparation of the vesicles, where the fusogens will bind non-covalently. When the lumen component is included in the medium for preparing the liposomes, frequently the liposomes will be washed after the liposomes have been prepared. One or more washings may be employed using appropriate buffer solutions, e.g. buffer used for preparation of the liposome, to remove the component from the surface of the vesicle.

To enhance the concentration of the lumen component, the liposomes may be combined in an aqueous medium comprising salts, particularly buffered medium, generally at a pH in the range of about 5 to 10. The salts may have ions which are mono- or polyvalent (singly or multiply charged), generally from about 1 to 3 charges. The ions may comprise buffering ions or non-buffering ions. Buffers may include Tris, phosphate, Hepes, Mops, or the like, particularly buffers dependent upon ammonium ion. Other salts include sodium chloride, potassium chloride, ammonium chloride, ammonium sulfate, sodium sulfate, lithium chloride, calcium chloride, and the like, particularly cations of Groups I and II of the Periodic Chart and ammonium ion. For the most part, the various ions at the concentrations employed will be physiologically acceptable for the purposes employed. Generally, the salt molarity will be at least about 25 mM, and not more than about 200 mM, usually in the range of about 25 to 100 mM. Generally sodium chloride and calcium chloride, individually or combined, will be present in the range of about 5 to 100 mM.

The liposomes are combined with an aqueous solution of the lumen component and incubated for at least about 0.1 h, usually at least about 0.2 h and generally not more than about 24 h, usually not more than about 12 h, conveniently not more than about 2 h. The temperature of the incubation can vary from about 4° C. to about 50° C., generally from about 10° to 30° C., conveniently at under ambient conditions. The particular temperature at which the incubation is carried out is not critical to this invention, although with some lumen components the lower portion of the temperature range (<20° C.) will be preferred. The washing of the liposomes is preferably at a relatively low temperature, preferably below about 20° C., more preferably below about 10° C., particularly in the range of about 0° to 10° C., more particularly 4° C. Conveniently, the washing may be carried out with the incubation medium in the absence of the lumen component.

The amount of the lumen component in the aqueous medium will generally be at least about 0.1 mM, more usually at least about 0.5 mM, and may be as high as 10 mM or more, depending on the lumen component, usually with nucleic acids, the lumen component will be not more than about 0.5 mM.

The liposomes may be stored in appropriate medium, which may or may not include the lumen component, depending upon whether leakage is of concern. Where the lumen component is present in the external medium, the liposomes will normally be washed before use. The fusogen may then be employed as appropriate to provide for fusion.

The liposomes may be administered in a wide variety of ways, depending upon the purpose for which they are employed. The liposomes may be administered by aerosol, parenterally, orally, by skin application, intravascularly, intraperitoneally, intramuscularly, and the like. The liposomes may be in an appropriate physiologically acceptable medium, as a paste, as a dispersion, and the like. Physiological mediums include aqueous mediums, saline solution and phosphate buffered solutions. The concentrations and dosage will vary widely, depending upon the mode of administration, the nature of the drug, the indication to be treated, the frequency of administration, the purpose of the administration, the nature of the host, and the like. Therefore the particular concentration and dosage will be determined empirically in accordance with conventional ways.

The subject compositions can be used for treating vertebrates, where the purpose of the administration may be for research, prophylaxis, therapy, initiating a physiological response, or the like. The compositions may be used for the treatment of humans or veterinary purposes, e.g. research and domestic animals. In many instances the subject compositions may be administered directly to the site to be treated, where the liposomes will provide for sustained release over an extended period of time. Alternatively, the liposomes may be administered into the blood stream, where the liposomes may concentrate at a particular site, particularly where the site has a member of a specific binding pair and the liposomes have the complementary or reciprocal member of the specific binding pair. The liposomes will then home to such site. Such compositions include antibodies, homing receptors, integrins, ligands for surface membrane protein receptors, etc.

The following examples are offered by way of illustration and not by way of limitation.

EXPERIMENTAL

Example 1

A. Preparation of Liposomes

Lipids were extracted from *E. coli*, following the procedure of Bligh and Dyer (Anal. Biochem. (1953) 18, 301–307). The polyphosphate-calcium salt was formed by precipitating polyphosphate (1 ml, 0.5 mM) with calcium chloride (0.5 ml, 4 mM) and centrifuging at 15,000 rpm for 20 min. Poly-hydroxybutyrate (10 mg/ml in chloroform) was added to the polyphosphate salt and dried overnight at 45° C. A lipid solution in chloroform (30:1 lipid/complex, molar ratio) was added and sonicated in the presence of buffer, Tris-HCl pH 7.2 (final lipid concentration 20 mM). The suspension was cooled and the fluorescence anisotropy recorded. The same procedure is followed to prepare vesicles without the complex. In this way, large multilamellar vesicles were prepared. The vesicles were filtered through an extruder in order to obtain large unilamellar vesicles.

The vesicle dispersion was transferred to an extrusion device (Sciema Technical Services Ltd., Richmond, B.C.) which extrudes the vesicles through standard 25 mm polycarbonate filters with 0.1 μm pore size (Nuclepore Corp., Pleasanton, Cal.). The vesicles in 2–5 ml, were injected into a central chamber above the polycarbonate filters and nitrogen pressure of 105–500 lb/in$^2$ employed, resulting in a flow rate of 20–60 ml/min, were collected and reinjected. The majority of the large unilamellar vesicles, (LUV) preparations were passed through 2 (stacked) filters 10 times.

B. The vesicles, 20 mM in phospholipids, were incubated with 1 mM ATP (5 μCi/ml) for different time periods at 37° C., centrifuged at 160,000 g for 20 min and washed with the incubation buffer at 4° C. Two conditions were employed: (1) incubation buffer of 1 mM NaCl; 50 mM Tris-HCl pH 7.2; (2) 1 mM NaCl, 50 mM Tris-HCl pH 7.2; 5 mM ammonium sulfate. The vesicle preparation was then counted in a scintillation counter before and after washing the vesicles and with vesicles prepared with and without the poly-hydroxybutyrate complex. According to Szoka A., Biochem. Biophys. Acta (1990) 263, 37–47, the trapped volume was 4%.

TABLE 1

| | % Counts | | | | | | | |
|---|---|---|---|---|---|---|---|---|
| | 1 | | | | 2 | | | |
| | without complex | | with complex | | without complex | | with complex | |
| time (min) | before wash | after wash | before wash | after wash | before wash | after wash | before wash | after wash |
| 1 | 9.2 | 0.1 | 8.9 | 0.1 | 9.2 | 0.1 | 9.2 | 1.7 |
| 5 | 9.1 | 0.3 | 9.1 | 0.3 | 9.1 | 0.3 | 9.3 | 2.4 |
| 10 | 8.9 | 0.2 | 9.0 | 0.1 | 8.9 | 0.2 | 10.8 | 4.6 |
| 15 | 8.7 | 0.2 | 9.0 | 0.1 | 9.0 | 0.1 | 12.6 | 6.5 |
| 30 | 9.0 | 0.1 | 8.6 | 0.2 | 8.9 | 0.3 | 17.5 | 7.3 |
| 60 | 9.1 | 0.3 | 8.7 | 0.1 | 9.2 | 0.2 | 20.3 | 7.8 |
| 120 | 9.2 | 0.2 | 3.0 | 0.2 | 9.1 | 0.1 | 21.7 | 7.9 |

Example 2

Following the procedure described previously, vesicles were prepared using either 60 mM *E. coli* lipid (1) or 60 mM of PC/PG (1:1; phosphatidyl choline/phosphatidyl glycerol)(2). The buffer employed was 50 mM Tris-HCl Ph 7.2, 5 mM ammonium sulfate, 10 mM NaCl. The solution had 1 mM ATP (5 μCi/ml). The vesicles were incubated and washed as previously described. In this case, the inner volume of the liposomes is 9%.

TABLE 2

| | % Counts | | | | | | | |
|---|---|---|---|---|---|---|---|---|
| | 1 | | | | 2 | | | |
| | without complex | | with complex | | without complex | | with complex | |
| time (min) | before wash | after wash | before wash | after wash | before wash | after wash | before wash | after wash |
| 1 | 10.1 | 0.1 | 9.7 | 0.6 | 9.8 | 0.1 | 9.4 | 1.4 |
| 5 | 9.7 | 0.3 | 9.8 | 1.2 | 9.7 | 0.3 | 9.6 | 2.3 |
| 10 | 8.6 | 0.2 | 10.4 | 1.7 | 8.5 | 0.2 | 11.9 | 4.5 |
| 15 | 9.3 | 0.4 | 10.7 | 2.4 | 9.4 | 0.3 | 13.5 | 7.4 |
| 30 | 9.2 | 0.1 | 11.3 | 3.6 | 9.7 | 0.4 | 18.1 | 9.6 |
| 60 | 9.3 | 0.3 | 11.2 | 3.4 | 9.4 | 0.3 | 20.7 | 9.5 |

Example 3

Following the procedure of Example 2, the procedure was varied by incubating and washing at (1) 4° C. or (2) 37° C. The lipid extracted from *E. coli* was employed. The following table indicates the results.

TABLE 3

| | % Counts | | | | | | | |
|---|---|---|---|---|---|---|---|---|
| | 1 | | | | 2 | | | |
| | without complex | | with complex | | without complex | | with complex | |
| time (min) | before wash | after wash | before wash | after wash | before wash | after wash | before wash | after wash |
| 1 | 9.6 | 0.2 | 9.7 | 1.5 | 9.8 | 0.2 | 9.6 | 0.1 |
| 5 | 9.7 | 0.3 | 9.4 | 2.3 | 9.6 | 0.3 | 10.3 | 0.2 |
| 10 | 8.6 | 0.1 | 12.1 | 4.8 | 10.1 | 0.1 | 8.9 | 0.3 |
| 15 | 9.0 | 0.2 | 14.0 | 7.9 | 9.7 | 0.2 | 10.1 | 0.1 |
| 30 | 9.1 | 0.3 | 17.9 | 10.1 | 9.6 | 0.3 | 9.6 | 0.2 |
| 60 | 9.4 | 0.2 | 19.8 | 10.4 | 10.2 | 0.1 | 9.5 | 0.1 |

Example 4

A DNA fragment of 1.2 kbp was labeled with $^{32}$p by the random oligo priming technique (Molecular Cloning: A Laboratory Manual, Sambrook et al. eds., Cold Spring Harbor Laboratories, Cold Spring Harbor, N.Y., 1988) and denatured for 10 min at 80° C. The single stranded DNA was incubated at 37° C. in Tris-Hcl Ph 7.2, 40 mM $CaCl_2$ with the vesicles prepared as described in Example 3, with and without the complex, for varying amounts of time, centrifuged at 160,000 g for 15 min at 3° C. and washed for 15 min in the incubation buffer. The samples were then counted in a scintillation counter.

The following table indicates the results.

TABLE 4

| | % Counts | |
|---|---|---|
| min | without complex | with complex |
| 15 | 0.09 | 0.97 |
| 30 | 0.13 | 1.63 |
| 60 | 0.09 | 3.36 |
| 120 | 0.06 | 6.30 |

EXAMPLE 5

The procedure in Example 4 was followed, except that the labeled $^{32}$P oligonucleotide fragment was treated with S1 endonuclease and the DNA fragments reprecipitated. The following table indicates the results.

TABLE 5

| | % Counts | |
|---|---|---|
| min | without complex | with complex |
| 15 | 0.79 | 1.05 |
| 30 | 0.95 | 2.24 |
| 60 | 1.13 | 4.85 |
| 120 | 0.09 | 9.10 |

EXAMPLE 6

The uptake of 1 Kb ladder probe DNA and plasmid DNA was determined by using 10 μg of ladder probe DNA resuspended in 40 μl TE (no phenol extraction) using the Gibco method employing T4 polymerase. For the plasmid labeling (rsv-luc) *E. coli* was employed from frozen stock and grown in 5 ml using 150 ml flask at 37° C. with 50 μCi$^{32}$P overnight. A miniprep was employed using the Quiagen method, obtaining about 20 μg, which was resuspended in 40 μl of TE. The DNA was tested by running 5 μl of each resuspended probe in 1% agar gel with TEA. Approximately 3–5 μg of plasmid and approximately 0.5 μg of ladder probe/5 μl was visualized with ethidium bromide. Large unilamellar vesicles (1,000 Å with or without the polyhydroxybutyrate complex) were resuspended in Tris-HCl pH 7.2 and 40 mM $CaCl_2$.

300 µl of the vesicle preparation and 5 µl of labeled 1 KB ladder (sp. activity 200,000 cpm/µl) or 300 µl of vesicle preparation and 8 µl of labeled plasmid preparation (sp.activity 9632 cpm/µl) were prepared as the incubation mixtures. For the labeled ladder probe DNA, there was one incubation for 1 h and one incubation for 2 h at 37° C. For the labeled plasmid there was one incubation for 2 h at 37° C. Parallel incubations were done to serve as DNase controls. After incubation, the incubation preparation was spun twice at 140,000 rpm in an ultracentrifuge for 10 min at 4° C. followed by washing with the incubation buffer. The samples were then resuspended in 25 µl of the same buffer and 6 µl aliquots of each sample were counted in a scintillation counter. Parallel samples were not counted until after the DNase treatment.

Parallel samples were treated with DNase to remove any DNA unincorporated in the vesicles. The protocol was to employ 20 µl of vesicle preparation, 2 µl of NEB 4(10x) buffer, 2 µl of DNase incubated at 37° C. for 50 min and spun in an ultracentrifuge for 15 min at 4° C. The supernatant was separated and the pellet resuspended in 25 µl of Tris buffer. 0.25 of the supernatant and resuspension (5 and 6 µl respectively) were counted in a scintillation counter.

All resuspended pellets were lysed by freezing with liquid nitrogen for 2 min and thawing. After lysis, 5 µl of 0.5M EDTA were added to parallel samples to inactivate DNase activity. The remaining unused labelled plasmid and ladder were divided into 2 aliquots and 1 aliquot was incubated with DNase as previously described. This provided controls for the function of DNase.

Gel electrophoresis was performed with a 1% agarose gel with TEA and ethidium bromide. The remaining vesicle preparation (19 µl) was loaded onto the gel with 4 µl of loading buffer, the electrophoresis run overnight and visualized by uv. The gel was then vacuum dried at room temperature for about 2 h and placed on film.

The following table represents the results.

| SAMPLE (pellet) | | Counts | % |
|---|---|---|---|
| 1kb ladder | liposome 60 min | 533 | 0.2 |
| | 120 min | 554 | 0.2 |
| | liposome + complex 60 min | 8901 | 3.6 |
| | 120 min | 15020 | 6.0 |
| | 60 min + DNase | 6592 | 2.6 |
| | (supernatant) 60 min + DNase | 2674 | 1.1 |
| | 120 min + DNase | 9680 | 3.9 |
| | (supernatant) 120 min + DNase | 4252 | 1.7 |
| plasmid | liposome 120 min | 87 | 0.1 |
| | liposome + complex 120 min | 4374 | 6.1 |
| | 120 min + DNase | 2723 | 3.7 |
| | (supernatant) 120 min + DNase | 881 | 1.2 |

The results suggest that the DNA could have been internalized into the liposomes, since it is protected from the action of DNase. The same result was observed with the 1 Kb ladder. In each case, in the absence of the liposome protection, all of the DNA was degraded, leaving a substantially blank lane.

It is evident from the above results, that the subject invention provides for uptake of the solutes in the lumen of a liposome. By providing for encapsulation of a wide variety of solutes, the liposomes can be used for more effective delivery of drugs, DNA, or other component. In this way, greater efficiencies in delivery can be achieved. The liposomes may be modified in a variety of ways, to enhance fusion with cellular membranes, to direct the liposomes to specific targets, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A liposome comprising a poly-β-hydroxybutyrate calcium polyphosphate complex in the membrane of lamellar forming phospholipids.

2. A liposome according to claim 1, wherein said phospholipids are at least 75 mole % of total lipids present in said liposome.

3. A liposome according to claim 2, wherein said phospholipids are from the membrane of a unicellular microorganism or synthetic phospholipids.

4. A liposome according to claim 3, wherein said poly-β-hydroxybutyrate is obtained from a unicellular microorganism.

5. A liposome according to claim 1, wherein the mole ratio of lipid to poly-β-hydroxybutyrate is in the range of about 10–60:1.

6. A liposome according to claim 1, comprising a nucleotide at a concentration of at least about 0.1 mM in the lumen of said liposome.

7. A liposome according to claim 1, comprising a nucleic acid at a concentration of at least about 0.1 mM in the lumen of said liposome.

8. A liposome according to claim 1 comprising a fusogen bound to the surface of said liposome.

9. A method for making a liposome according to claim 1 comprising:

sonicating an intimate mixture of lipids comprising at least about 80 mole % phospholipids and a poly-β-hydroxybutyrate calcium polyphosphate complex in an aqueous medium for sufficient time for liposomes to form.

10. A method according to claim 9, comprising the additional step of extruding said liposomes through a membrane having pores of from about 0.1 to 1µ.

11. A method of delivering a compound to a site of a host, said method comprising:

administering a liposome according to claim 1 comprising said compound in the lumen of said liposome to said site or to the blood stream of said host upstream from said host.

12. A method according to claim 11, wherein said site comprises a member of a specific binding pair and said liposome has associated with the membrane of said liposome the complementary member of said specific binding pair.

* * * * *